United States Patent
Eckles et al.

(10) Patent No.: US 9,678,050 B2
(45) Date of Patent: Jun. 13, 2017

(54) MULTI-FUNCTIONAL PIEZO ACTUATED FLOW CONTROLLER

(71) Applicant: LI-COR, Inc., Lincoln, NE (US)

(72) Inventors: Robert D. Eckles, Malcolm, NE (US); Mark Johnson, Hickman, NE (US); Tyler Anderson, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 457 days.

(21) Appl. No.: 14/447,352

(22) Filed: Jul. 30, 2014

(65) Prior Publication Data

US 2016/0033461 A1    Feb. 4, 2016

(51) Int. Cl.
     *G01N 33/00*      (2006.01)

(52) U.S. Cl.
     CPC ....... *G01N 33/0031* (2013.01); *G01N 33/004* (2013.01)

(58) Field of Classification Search
     CPC .......................... G01N 33/0031; G01N 33/004
     See application file for complete search history.

(56) References Cited

U.S. PATENT DOCUMENTS

| 6,095,175 | A | 8/2000 | Miller et al. |
| 8,610,072 | B2 | 12/2013 | Genty et al. |

(Continued)

FOREIGN PATENT DOCUMENTS

CN      203719691 U      7/2014

OTHER PUBLICATIONS

International Search Report and the Written Opinion in International Patent Application No. PCT/US2014/042290 (Oct. 16, 2015).

*Primary Examiner* — Paul West
(74) *Attorney, Agent, or Firm* — Leydig, Voit & Mayer, Ltd; Gerald T. Gray

(57) ABSTRACT

Multi-functional piezo-actuated flow control systems and methods for use in gas exchange analysis systems such as photosynthesis measurement systems. A fluid valve assembly module includes a housing structure including a plurality of ports and a plurality of fluid passageways interconnecting the ports, and a plurality of piezo-actuated valves in fluid communication with the fluid passageways, each valve including a piezo element that controls flow along a passageway, wherein the passageways and valves are arranged within the housing structure so as to define a fluid control module, which includes a flow swapping component, a flow splitting component and a flow pressurization component. The flow swapping component has first and second inlets and first and second output ports and is configured to receive a first fluid flow at the first inlet and a second fluid flow at the second inlet and in a first operational mode to direct the first fluid flow to the first output port and the second fluid flow to the second output port, and in a second operational mode to direct the first fluid flow to the second output port and the second fluid flow to the first output port. The flow splitting component has an input port, a third output port and a first outlet and is configured to receive an input fluid flow at the input port and to control an amount of the input fluid flow provided to the third output port and to the first outlet in a continuously adjustable manner, wherein the first outlet is fluidly connected to the first inlet of the flow swapping component and the third output port is adapted to be fluidly coupled with an external reservoir. The flow pressurization component has an entry port in fluid communication with a second outlet and is configured to receive a third fluid flow at the entry port and to control the pressure of the third fluid flow at the second outlet, wherein the second outlet is fluidly connected to the second inlet of the flow swapping component and the entry port is adapted to be fluidly coupled with the external reservoir.

30 Claims, 7 Drawing Sheets

(56) References Cited

U.S. PATENT DOCUMENTS

2010/0262382 A1    10/2010   Lighton
2012/0073355 A1     3/2012   Johnson et al.
2012/0181432 A1     7/2012   Welles

MULTI-FUNCTIONAL PIEZO ACTUATED FLOW CONTROLLER

BACKGROUND

The present invention relates generally flow control systems and methods, and more particularly to multi-functional piezo-actuated flow control systems and methods for use in gas exchange analysis systems such as photosynthesis measurement systems.

Systems for measuring plant photosynthesis and transpiration rates can be categorized as open or closed systems. For open systems, the leaf or plant is enclosed in a chamber, and an air stream is passed continuously through the chamber. $CO_2$ and $H_2O$ concentrations of chamber influent and effluent are measured, and the difference between influent and effluent concentration is calculated. This difference is used, along with the mass flow rate, to calculate photosynthesis ($CO_2$) and transpiration ($H_2O$) rates. For closed systems, the leaf or plant is enclosed in a chamber that is not supplied with fresh air. The concentrations of $CO_2$ and $H_2O$ are continuously monitored within the chamber. The rate of change of this concentration, along with the chamber volume, is used to calculate photosynthesis ($CO_2$) and transpiration ($H_2O$) rates.

In both open and closed systems, it is important that the leaf or plant be the only source or sink of both $CO_2$ and $H_2O$. $CO_2$ or $H_2O$ concentration changes not caused by the plant are each a measurement error. These errors can be empirically compensated, for example as described in the LI-COR Biosciences LI-6400 User Manual (pp. 4-43 thru 4-48; included herein as Appendix A). Some instrument users may not understand the significance of these corrections, and neglect them.

Both open and closed systems contain a circuit of pneumatic components (e.g., pumps, valves, chambers, tubing, analyzers, etc.). When $CO_2$ and $H_2O$ concentrations are dynamically changing, sorption on these components can provide an apparent $CO_2$ or $H_2O$ source and/or sink. Under steady-state conditions, sorption is not an active source or sink, and parasitic $CO_2$ and $H_2O$ sources and/or sinks can be attributed to bulk leaks and diffusion.

Bulk leaks are driven by pressure differentials between the system and the ambient environment. Proper system design and construction, along with inherently low operating pressures, generally minimize parasitic sources and sinks due to bulk leaks. Diffusion is driven by constituent gas ($CO_2$ and $H_2O$) concentration gradients between the system and ambient environment. Any time constituent gas concentrations inside the system are significantly different than ambient conditions, the diffusion potential increases. Metals, in nearly any practical working thickness, generally provide an outstanding diffusion barrier to gases. Practically, however, nonmetallic materials are always required. For example, to provide a seal between metallic materials, gaskets and O-rings are used Flexible tubing which connects the sensor head to other system components is an example of functional capabilities which cannot be reasonably achieved with metals.

In open photosynthesis systems, a conditioned air stream is typically split into two streams. A first flow path (known as reference) passes through a gas analyzer (e.g., Infra-Red Gas Analyzer or IRGA) which measures constituent gas concentrations ($CO_2$ and $H_2O$). The second flow path (known as sample) passes through a sample chamber (leaf chamber) in which gas exchange occurs. This second sample flow path exits the chamber and enters a second gas analyzer (e.g., IRGA). The difference between the sample and reference gas concentrations is used to calculate photosynthesis ($CO_2$) and transpiration ($H_2O$). As photosynthesis and transpiration measurements are based on concentration differences in these two gas streams, the accuracy in measuring the difference is more critical than measuring the absolute concentration of either. Diffusive parasitic sources and/or sinks present in the tubing, connectors, and fittings that supply the head with the sample and reference gas streams can compromise measurement accuracy. Typical systems for controlling fluid flow require control of high pressure flows and tend to have high power and heat dissipation concerns. Additionally, heating effects caused by various components in the fluid pathway, such as valves and associated control electronics components can cause noticeable errors in measurements. It is difficult to measure, and correct for, such heat dissipation in these systems.

Therefore it is desirable to provide systems and methods that minimize the impact of heat diffusion and that help overcome the above and other problems.

BRIEF SUMMARY

The present invention relates generally flow control systems and methods, and more particularly to multi-functional piezo-actuated flow control systems and methods for use in gas exchange analysis systems such as photosynthesis measurement systems.

According to an embodiment, a fluid valve assembly module (or flow control assembly module) is provided that typically includes a housing structure including a plurality of ports and a plurality of fluid passageways interconnecting the ports, and a plurality of piezo-actuated valves in fluid communication with the fluid passageways, each valve including a piezo element that controls flow along a passageway, wherein the passageways and valves are arranged within the housing structure so as to define a fluid control module. The fluid control module typically includes a flow swapping component, a flow splitting component and a flow pressurization component. The flow swapping component typically has first and second inlets and first and second output ports and is typically configured to receive a first fluid flow at the first inlet and a second fluid flow at the second inlet and in a first operational mode to direct the first fluid flow to the first output port and the second fluid flow to the second output port, and in a second operational mode to direct the first fluid flow to the second output port and the second fluid flow to the first output port. The flow splitting component typically has an input port, a third output port and a first outlet and is typically configured to receive an input fluid flow at the input port and to control an amount of the input fluid flow provided to the third output port and to the first outlet in a continuously adjustable manner, wherein the first outlet is fluidly connected to the first inlet of the flow swapping component and the third output port is adapted to be fluidly coupled with an external reservoir. The flow pressurization component typically has an entry port in fluid communication with a second outlet and is typically configured to receive a third fluid flow at the entry port and to control the pressure of the third fluid flow at the second outlet, wherein the second outlet is fluidly connected to the second inlet of the flow swapping component and the entry port is adapted to be fluidly coupled with the external reservoir.

In certain aspects, the flow swapping component includes two piezo elements, wherein the flow splitting component includes a single piezo element and wherein the flow pressurization component includes a single piezo element, in certain aspects, each piezo element includes a cantilevered piezoelectric element that bends in response to an applied voltage signal. In certain aspects, the piezo elements are arranged in a substantially planar side-by-side relationship. In certain aspects, the piezo elements are arranged in a vertical stacked relationship. In certain aspects, the fluid control module receives control signals from a control circuit external to the fluid control module. In certain aspects, the fluid valve assembly module further includes a flow sensor connected between the third output port and the reservoir, wherein the flow sensor provides feedback signals to the control circuit.

According to another embodiment, a gas exchange analysis system is provided that typically includes a gas source, a chamber defining a measurement volume for analysis of a sample, a first gas analyzer, a second gas analyzer, and a valve assembly module including a housing structure having a plurality of ports that fluidly interconnect the gas source, the chamber, the first gas analyzer and the second gas analyzer, wherein the valve assembly module includes a plurality of passageways interconnecting the ports and a plurality of valves that control fluid flow along the passageways. The passageways and valves are typically arranged within the housing structure in a manner that defines various functional components. In certain embodiments, the sub-components include a flow splitting component, a flow pressurization component and a flow swapping component, wherein the flow splitting component receives an input fluid flow from the gas source and is configured to adjust an amount of the input fluid flow provided to both the flow swapping component as a first fluid flow and to the chamber, wherein the flow pressurization component is configured to control of a pressure of a second fluid flow along a flow path from the chamber to the flow swapping component, and wherein the flow swapping component receives the first fluid flow and the second fluid flow along separate flow paths and that is configured to controllably swap or interchange the first and second fluid flows between the first and second gas analyzers.

In certain aspects, the flow splitting component has an input port fluidly coupled with the gas source, a first output port fluidly coupled with the chamber and a first outlet fluidly connected to a first inlet of the flow swapping component, wherein the flow splitting component is configured to adjust the amount of the input fluid flow provided to both the first output port and the first outlet. In certain aspects the flow pressurization component has an entry port in fluid communication with the chamber, and a second outlet fluidly connected to a second inlet of the flow swapping component, wherein the flow pressurization component is configured to receive a second fluid flow from the chamber at the entry port and to control a pressure of the second fluid flow at the second outlet. In certain aspects, the flow swapping component includes the first and second inlets, and second and third output ports fluidly coupled with the first and second gas analyzers, respectively, wherein the flow swapping component is configured to receive the first fluid flow at the first inlet and the second fluid flow at the second inlet and in a first operational mode to direct the first fluid flow to the second output port and the second fluid flow to the third output port, and in a second operational mode to direct the first fluid flow to the third output port and the second fluid flow to the second output port.

In certain aspects, the flow swapping component includes two piezo elements, wherein the flow splitting component includes a single piezo element and wherein the flow pressurization component includes a single piezo element. In certain aspects, each piezo element includes a cantilevered piezoelectric element that bends in response to an applied voltage signal. In certain aspects, the piezo elements are arranged in a substantially planar side-by-side relationship. In certain aspects, the piezo elements are arranged in a vertical stacked relationship. In certain aspects, the fluid control module receives control signals from a control circuit external to the fluid control module. In certain aspects, the fluid valve assembly module further includes a flow sensor connected between the third output port and the reservoir, wherein the flow sensor provides feedback signals to the control circuit.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

The following further illustrates the multi-functional piezo-actuated flow control systems of the present disclosure, but, of course, should not be construed as in any way limiting its scope.

Figure 1:
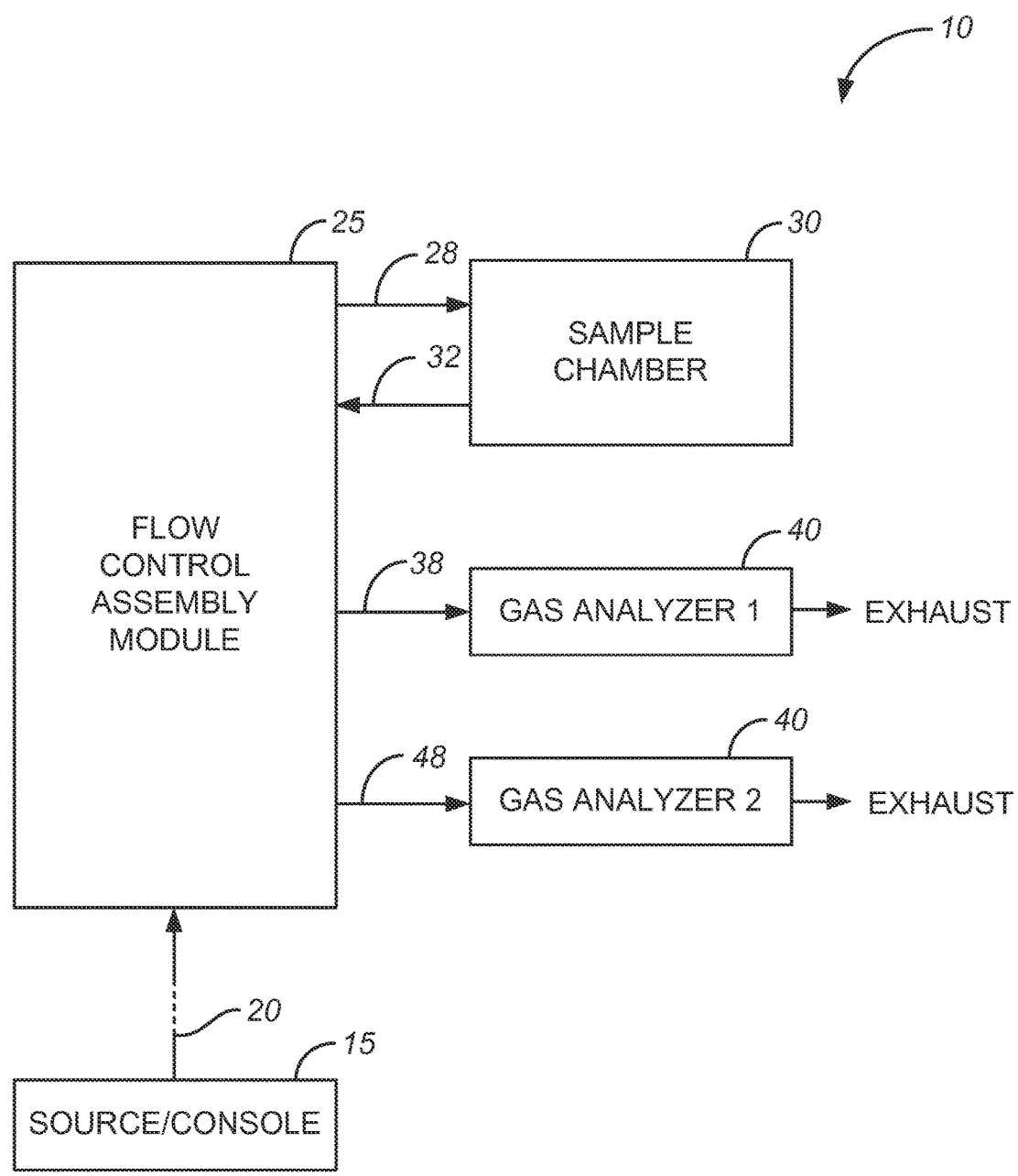
FIG. 1 illustrates an embodiment of a gas exchange analysis system (GEAS) according to an embodiment.

FIG. 1 illustrates an embodiment of a gas exchange analysis system (GEAS) 10 according to an embodiment. GEAS 10 in one embodiment includes a console or source of gas 15, a flow control assembly module 25, a sample chamber 30 (e.g., leaf chamber), a first gas analyzer 40 and a second gas analyzer 50. Console or gas source 15 includes one or more reservoirs of one or more gases and gas conditioning components. For example, in the context of photosynthesis and transpiration measurements, gas sources would include reservoirs of $CO_2$ and $H_2O$, and conditioning equipment for conditioning each gas concentration. A flow path 20 connecting source 15 with flow control assembly module 20 typically includes flexible tubing and connectors and can include various components in the flow path to appropriately condition the gas stream. Flow control assembly module 20 receives a stream of gas from source 15 and directs some or all of the received source input flow to sample chamber 30, receives a flow of exhaust gas from chamber 30 and controllably provides some or all of the received source input flow and chamber exhaust flow to first gas analyzer 40 and to second gas analyzer 50 as will be described in more detail below. First gas analyzer 40 and second gas analyzer 50 might each include an Infra-Red Gas Analyzer (IRGA), as is known in the art, or other gas analyzer.

It should be appreciated that the relative positioning of ports and components can be varied from that shown.

Flow control assembly module 25 includes a plurality of passageways and a plurality of active valve elements, including valves with active valve actuators, arranged in a manner that facilitates conditioning and provision of gas flows received from the various inputs to the various outputs in a controlled manner. "Active" devices or components include those that can be controlled electronically by a computer, controller, or other machine. Active devices or components often can be adjusted in real-time automatically without intervention by a human operator. In certain embodiments, the active valve elements include piezoelectric or piezoresistive (hereinafter also termed "piezo") elements.

A piezo element is typically actuated by application of a voltage signal. A piezo valve includes a valve body defining an internal volume and having at least one port for introducing fluid therethrough, at least one valve seat proximal the port for allowing the fluid to pass therethrough, a piezo bender plate having a fastened end and a distal end proximal to the valve seat and including a mating component that mates with the valve seat. A circuit or circuit board supplies an electric voltage signal to the piezo bender plate thereby straining the bender plate and moving the distal end in a direction toward or away from the valve seat, depending on the applied voltage, to thereby open or close the port. For proportional valves the applied voltage controls the distance the distal end travels and hence a rate of fluid flow through the port.

Technical advantages of using a piezoelectric valves include that piezoelectric elements can operate with very low power consumption, which is beneficial for battery-powered instruments. The physical size of piezoelectric valves is relatively small, and geometries of piezo actuators are favorable for small instruments.

Figure 2:
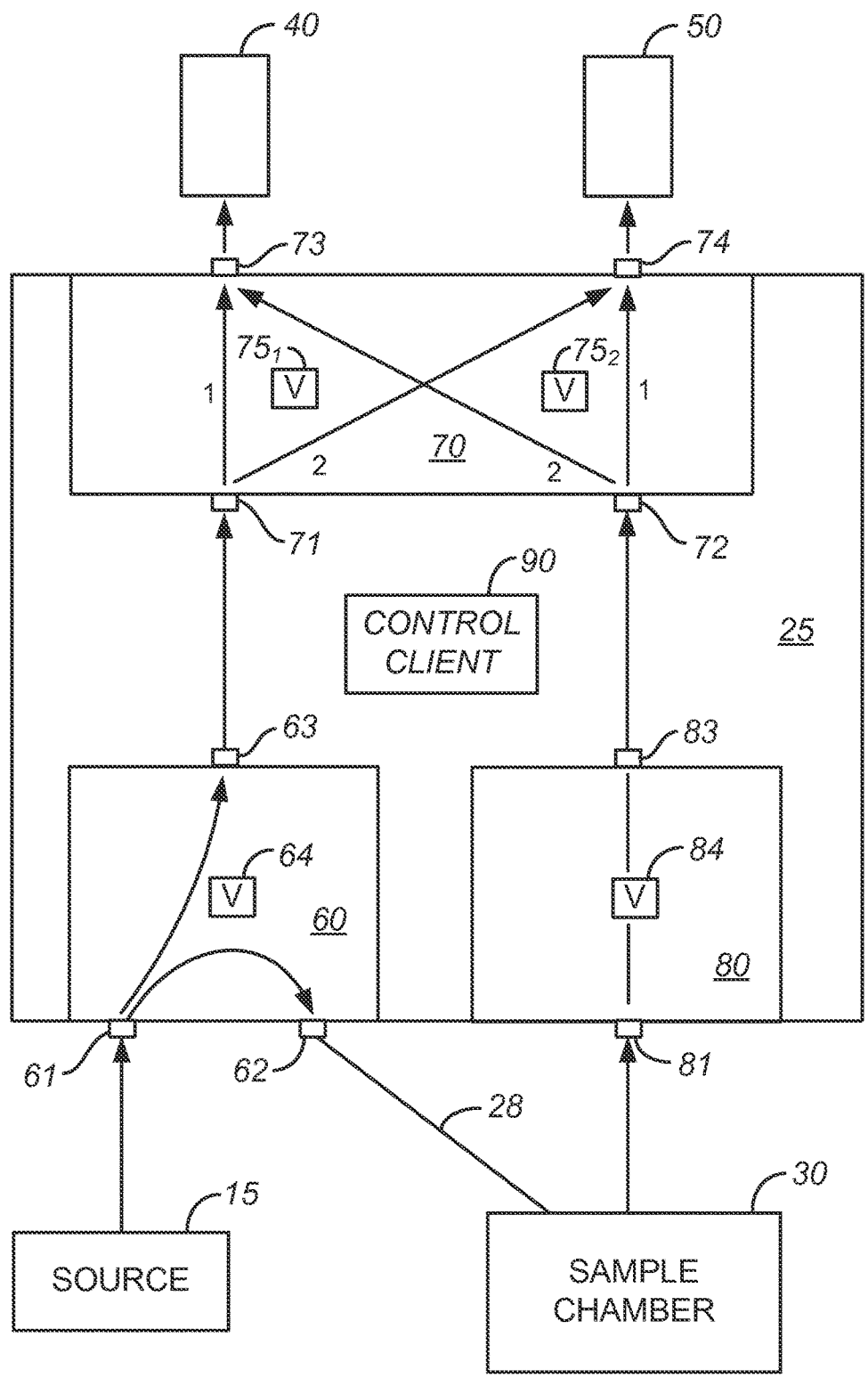
FIG. 2 illustrates a functional embodiment of a flow control assembly module (FCAM) according to an embodiment.

FIG. 2 illustrates a functional embodiment of a flow control assembly module (FCAM) 25 according to an embodiment. In the example shown, flow control assembly module 25 is configured to serve three functions: proportional flow splitting, flow swapping between 2 inlet ports and 2 output ports, and pressurization control of a flow stream. As shown, flow control assembly module 25 is configured with three functional modules: flow splitting component 60, flow swapping component 70 and flow pressurization module 80. A feedback control circuit 90 provides control signals to the various active components of FCAM 25, e.g., voltage control signals to control operation of the various valves in FCAM 25 and to adjust the various valve settings as required based on user input and/or feedback signals provided by various components of FCAM 25. In certain aspects, feedback control circuit 90 includes an intelligence module such as one or more microprocessors or ASICs or other integrated circuit device(s). Feedback control circuit may be located internal to FCAM 25 as shown (e.g., with electrical connectors to external control equipment, user input device, etc.), external to FCAM, e.g., with various electrical signal lines communicating with the various components of FCAM 25, or may include modules internal and external to FCAM 25.

As will be used herein, for port designation nomenclature, "inlet" port and "outlet" port generally indicate ports that are coupled with internal components or devices of FCAM 25, whereas "input" port and "output" port and "entry" port generally indicate ports that are coupled with components or devices external to FCAM 25. It should be appreciated, however, that any port may be coupled with an internal or an external (to FCAM 25) component or device.

In one embodiment, the flow splitting component or mechanism 60 is configured to receive a gas flow at an input port from an external source, e.g., gas source 15, and variably split the received input flow of gas into two different flows. In particular, the flow splitting mechanism 60 is configured to receive a gas flow at the input port 61 from an external source (gas source 15) and to variably split or provision the received flow an output port 62 and to an outlet port 63 as shown in FIG. 2. The output port 62 is fluidly coupled via a flow path 28 with the sample analysis chamber 30 and the inlet port 63 is fluidly coupled with an inlet port 71 of flow swapping component 70. The flow splitting mechanism 60 varies the ratio or proportion of the input flow of gas provided to the output port and the outlet port. In certain aspects, the flow splitting mechanism 60 is configured to adjust the flow ratio in a continuously variable manner such that the gas flow can be controllably, and continuously, varied to provide a flow range of between about 0% to 100% to the output port 62 and the remaining 100% to 0% to the outlet port 63. For example, the flow splitting mechanism can be controlled via a control signal to split the flow 25% to one of the output port 62 or outlet port 63 and 75% to the other port, or 50% to one port and 50% to the other port.

In one embodiment, flow splitting mechanism 60 includes a piezoelectric flow splitting valve 64 configured to variably split the input gas flow received at input port 61 to output port 62 and to outlet port 63. The flow splitting valve 64 operates as a 3way proportional valve, but can also function as a 3/2 valve (the 3/2 nomenclature denotes a valve with three ports and 2 operating positions (e.g., on-off device), responsive to a voltage control signal received from control circuit 90. In certain aspects, the piezo flow splitting device includes a piezo actuator having a first end secured within the device and a second end located proximal both the output port 62 and the outlet port 63, and electrical contacts for providing a control potential to the actuator to control the position of the second end relative to the output and outlet ports and thereby control the flow resistances and the flow ratio to these ports. For example, in certain aspects, an applied control potential controls the second end to adjust the position of the second end relative to the output and outlet ports such as to controllably adjust, and continuously in real time, a flow ratio of between about 0% to 100% to the output port 62 and concomitantly between about 100% to 0% to the outlet port 63. In one embodiment, the actuator includes a metal strip coated on both sides with a piezo-bender material. In certain aspects, the piezo-bender material includes lithium tantalite or other piezo-resistive material known to one skilled in the art.

Output port 62 is fluidly coupled with an input of enclosed sample chamber 30 which defines a measurement volume for analysis of a sample. An output port of sample chamber 30 is fluidly coupled with input port 81 of flow pressurization component 80.

In one embodiment, flow pressurization component or mechanism 80 is configured to receive a gas flow at entry port 81 and provide a controlled pressure of the received gas flow to outlet port 83. In particular, flow pressurization mechanism 80 is configured to control a pressure of the flow received from sample chamber 30 (and thereby control the pressure of fluid in the chamber 30) and provide the controlled flow to outlet port 83 which is fluidly connected to inlet port 72 of flow swapping component 70.

In one embodiment, flow pressurization component 80 includes a piezoelectric flow pressurization valve configured to control the pressure of the input gas flow received at entry port 81 and provided to outlet port 83. The flow pressurization valve operates as a 2-way proportional valve, but can also function as a 2/2 valve (the 2/2 nomenclature denotes a valve with two ports and two operating positions), responsive to a voltage control signal received from control circuit 90.

In one embodiment, flow swapping component or mechanism 70 includes two or more match valves 75 configured to receive a first gas flow at inlet port 71 and a second gas flow at inlet port 72 and to provide each of the first and second gas flows to either of the first output port 73 and the second output port 74 in a controlled manner. In particular, flow swapping component or mechanism 70 is configured to receive a first gas flow at inlet port 71 and a second gas flow at inlet port 72 and to provide the first and second gas flows to the first output port 73 and second output port 74, respectively, when in a first operational mode or to the second output port 74 and first output port 73, respectively, when in a second operational mode.

In one embodiment, flow swapping component 70 includes two independent piezo valves 75, each configured to operate as a 3/2 valve responsive to a voltage control signal received from control circuit 90.

First gas analyzer 40 is fluidly coupled with first output port 73 and second gas analyzer 50 is fluidly coupled with second output port 74. Each gas analyzer may include an infra-red gas analyzer (IRGA) or other gas analyzer configured to measure a concentration of a gas in the gas flow received from the respective output port. Data representative of the gas analyzer measurements can be provided from the gas analyzers to a processing module (not shown).

Figure 3:
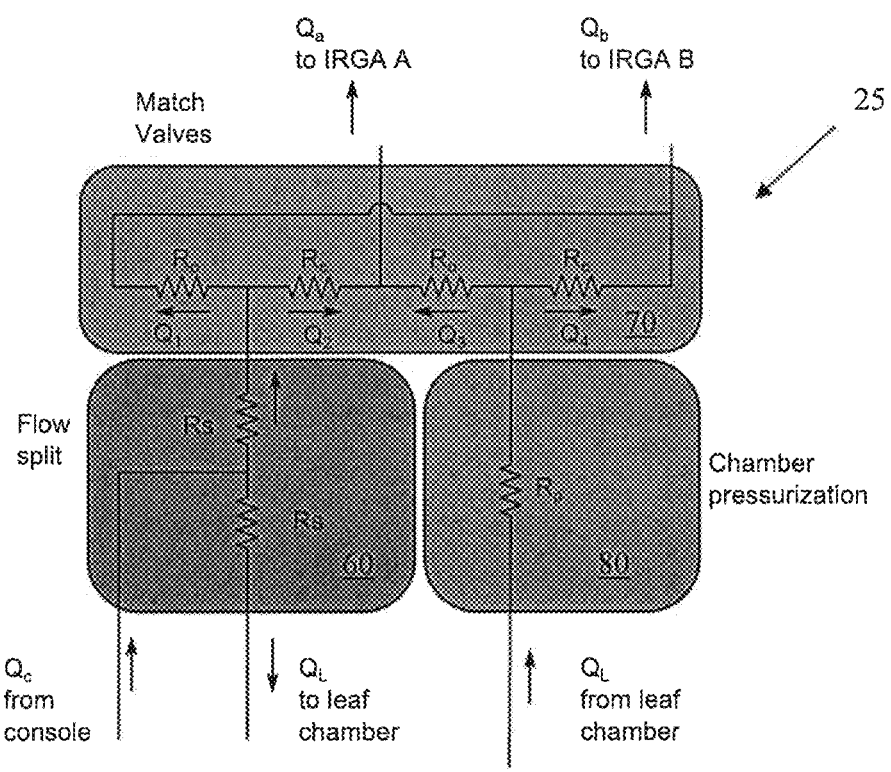
FIG. 3 is a schematic representation of the flow paths and blocks defining the three different functions of the piezo valves of the embodiment shown in FIG. 2.

FIG. 3 is a schematic representation of the flow paths and blocks defining the three different functions of the piezo valves of the embodiment shown in FIG. 2. Each R represents an interface between a piezo surface and orifice (which is typically directly connected to a port, possibly through an additional length of passageway). The piezo bimorphs or benders can be actuated to change the distances between piezo surfaces and orifices to vary the flow resistances (R values). Arrows represent the direction of gas flow through the system. Pressure can be treated as a function of flow rate, Q. (e.g., $P=R(Q)$) which is a notation for analyzing the fluid diagram. Valve performance can be expressed as the function R or $P=R(Q)$. Generally, R is second order, but linear approximations are sufficient. Under linear approximations the system is analogous to an electrical system with high and low resistances such that $P=R*Q$. This provides a way of expressing the partial pressure at either IRGA as a function of the partial pressures at the inlets. With sufficiently high resistance (e.g., valve closed) and sufficiently low resistance (e.g., valve open), cross-talk between channels becomes very small.

In certain embodiments, the piezo valves provide for passage of fluid with a low pressure drop and with low power dissipation. For example, in some embodiments, pressure drop when open is about 8 Pa @ 2 sLpm, total system pressure drops are about 50 Pa @ 2 sLpm, and maximum sealing pressures when closed are about 7 kPa for the match valve and 35 kPa for the flow split mechanism. Power dissipation is less than or equal to about 0.4 W, which advantageously does not amount to much of a temperature rise as most of the heat generating components are away from the gas stream.

In one embodiment, a flow meter (not shown) is coupled along a flow path between the output port 62 of the flow splitting component and the input of the sample chamber, the flow meter being adapted to measure a flow rate in the flow path. Feedback control circuit 90 is adapted to control the piezo flow splitting device to adjust a ratio of gas flow to the output port 62 and outlet port 63 responsive to a flow rate signal received from the flow meter, and various control parameters, e.g., parameters input by a user. A closed loop feedback controller for a flow splitter has been shown to have superior performance for gas exchange analysis systems that measure delicate photosynthesis affects of real-world plants. The flow on one side of a flow split into a leaf measurement chamber should be precisely known and controlled in order for evapotranspiration to be accurately measured within the chamber. Flow rate is one of the parameters of a leaf photosynthesis measurement. A flow splitter without feedback (i.e., open loop) might drift because conditions in the leaf chamber might change. The changing conditions can include temperature, partial pressures of certain gases, etc. These changes can include a pressure change that could affect flow rate through the chamber.

In some embodiments, it is desirable to adjust the amount of flow going into the leaf measurement chamber to accommodate different measurement conditions. However, since the amount of flow before the flow split is usually constant, changing the split ratio has been found to be a good way to regulate and control the flow to the sample chamber. One can control the flow into the sample chamber because it should be precisely known and regulated. Excess flow that is left over can be used for the reference path. Also, having the flow splitter located very close to or otherwise proximate to the chamber paths has been found to largely eliminate adsorption effects of the chamber, hose, and fitting walls.

In one embodiment, the system also includes a processing module, and/or is communicably coupled with a remote processing module, communicably coupled with the first and second gas analyzers, configured to receive gas concentration measurements from the gas analyzers and to provide data processing and display capabilities. The processing module(s) are also communicably coupled with the control circuit 90 to provide additional system control and to receive additional system data. The processing module(s) can receive gas measurement data and display gas concentration results. The results (data) can be output, displayed or otherwise provided to another computing system or device for further manipulation. In certain aspects, the gas includes $CO_2$ and/or $H_2O$.

In certain aspects, a flow volume, including the measurement volume in the sample chamber 30 and the flow path through the various components, is sufficiently small such as to reduce the time required to reach a steady state of gas concentrations in the flow volume when a flow ratio to the flow path is adjusted in the flow splitting mechanism. For example, the measurement volume might be on the order of 1 mL to 10 mL to about 1000 mL, such that the flow path including the flow volume between the flow splitting device and the first IRGA 40 and/or second IRGA 50 might be smaller than, or on the order of, about 20 mL to about 1000 mL.

Figure 4:
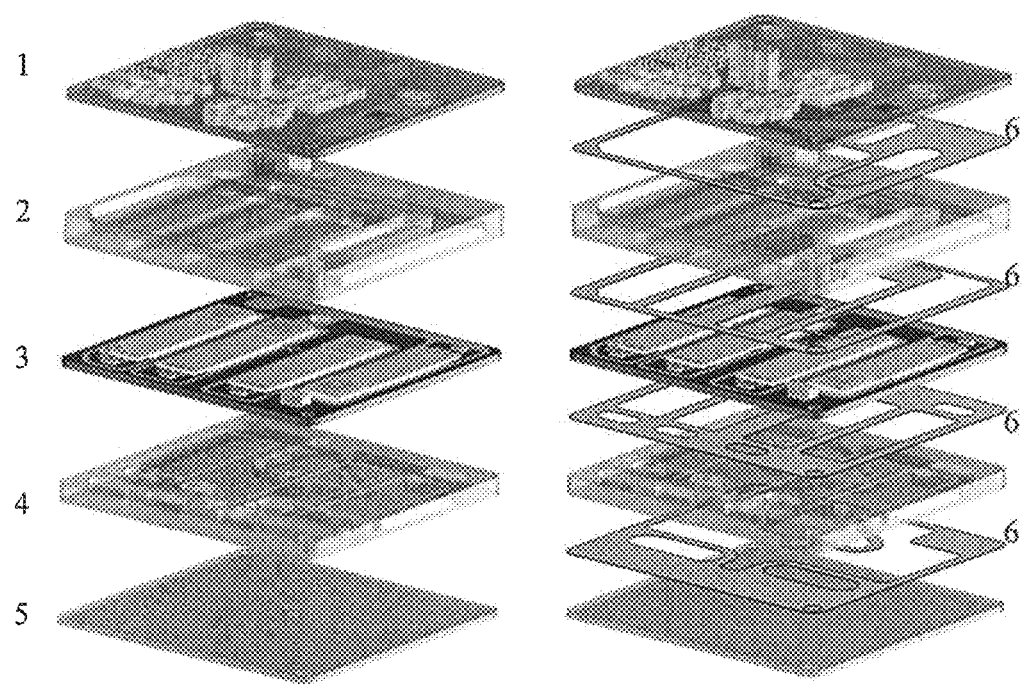
FIG. 4 is a schematic diagram of machined component layers of a flow control assembly module according to an embodiment.
Figure 5:
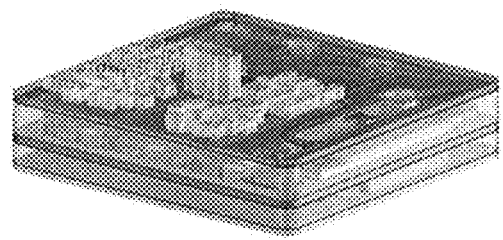
FIG. 5 is a schematic diagram of a packaged flow control assembly module according to FIG. 4.

FIG. 4 illustrates a schematic diagram of machined component layers of a flow control assembly module 25 according to an embodiment. Top layer 1, as shown, includes various control and interface electronic components. Layer 2 includes machined portions of passageways, layer 3 includes a body including a plurality of piezo bender elements, and layer 4 as shown is a machined part that may include additional passageways or portions of passageways. Layer 4 may optionally include all, or additional, control and/or interface circuitry elements. Combination of layers 2 and 3 produces a housing structure including valve bodies, ports and flow passageways, for example configured to implement the functionality shown and described with reference to FIGS. 1-3. When all layers are combined a housing structure is formed resulting in a flow control assembly module as shown in FIG. 5, which is a schematic diagram of a packaged flow control assembly module 25 according to FIG. 4. All or portions of the control and interface circuitry on the various layers define the control circuit 90. In certain aspects, the piezo elements (e.g., piezo benders) are arranged in a substantially planar side-by-side relationship as shown in FIG. 4 (e.g., layer 3). In other embodiments, some or all piezo elements are arranged in a vertical, stacked relationship.

The layout of the flow path allows for easy assembly since all layers reference off each other for alignment. Gap spacing between orifices and sealing surfaces are controlled through the machined parts. All machined parts are limited to 2 sided machining, which reduces the number of machine setups and helps reduce manufacturing complexity. Mold-in-place, polyurethane and vinyl gaskets 6 are useful options for sealing between each of the layers and reduce assembly time.

Bimorph piezo benders are preferably used as the actuator against a fluid port, e.g. against a valve seat. The actuators are able to seal and divert fluid flow to different areas within the assembly. Flow paths are created around the actuators using a "lamination" concept. As shown in FIG. 4, the piezo actuators are sandwiched between 4 layers: 2 machined parts on one side and 1 machined part and 1 circuit board on the other (top in FIG. 4) side of machined parts, 2 on each side. The piezo bimorphs can be actuated to change the distances between piezo surfaces and orifices to vary the flow resistances (R values).

Figure 6:
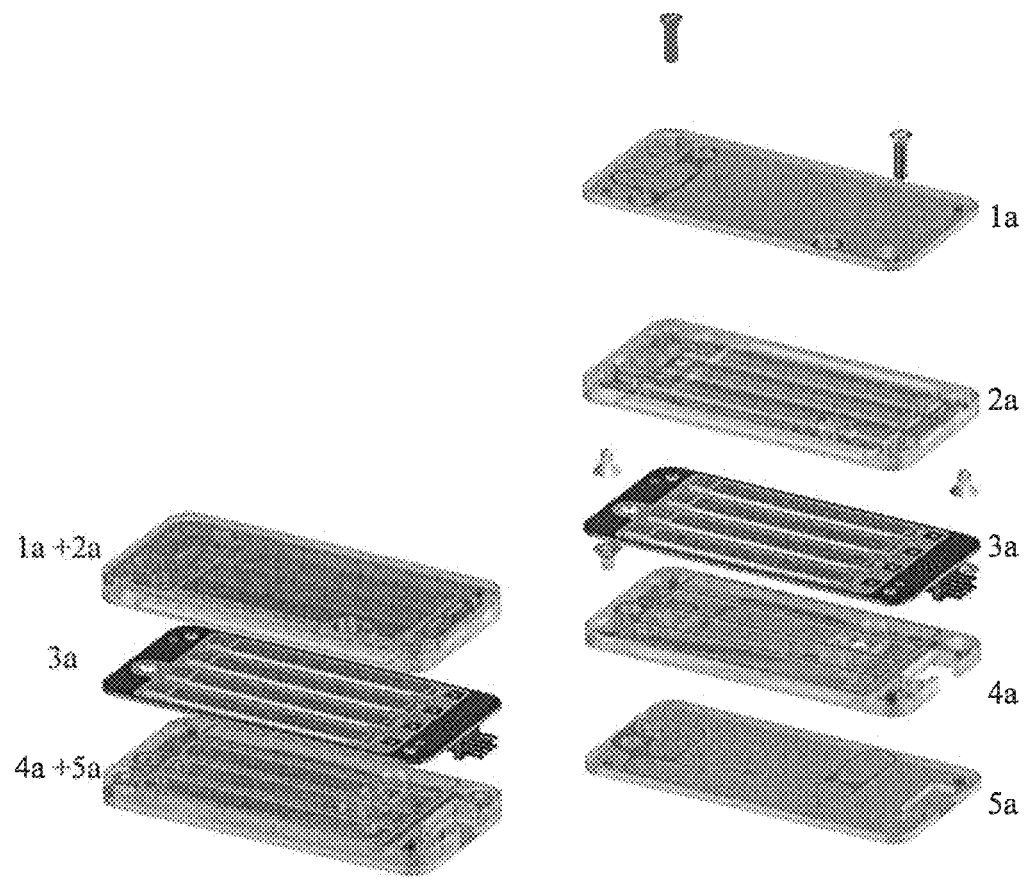
FIG. 6 is a schematic diagram of machined component layers of a flow control assembly module according to an embodiment.

FIG. 6 is a schematic diagram of machined component layers of a flow control assembly module 25 according to an embodiment. Top layer 1a, as shown, includes a machined housing plate. Layer 2a includes machined portions of passageways, layer 3a includes a body including a plurality of piezo bender elements, and layer 4a includes additional portions of passageways. Layer 5a includes another machined housing plate. Layer 3a also includes interface circuitry, e.g., for communicating or interfacing with an off-module control circuit 90. Combination of layers 1a-5a produces a housing structure including valve bodies, ports and flow passageways, for example configured to implement the functionality shown and described with reference to FIGS. 1-3. In The embodiment shown in FIG. 6, amplifier and control electronics can be integrated into one or more layers to provide flow control and interface to the center actuator board layer 3a via a board to board connector. This embodiment can include a MEMS-based flow sensor on the outlet that leads to the sample chamber. In certain aspects, fasteners and gaskets 6 may be replaced with die-cut VHB tape that serves as a gasket and/or a fastener. In certain aspects, the piezo elements are bonded in place using a conductive adhesive. Alternatively a structural epoxy with wire soldering can be used to secure piezo elements in place proximal circuit boards and other elements.

Figure 7:
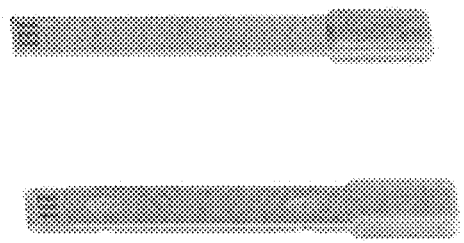
FIG. 7 illustrates an example of a piezo actuator useful in the flow control assembly module according to an embodiment.

FIG. 7 illustrates an example of a piezo actuator useful in the flow control assembly module 25 according to an embodiment. As shown, an overmold of gasket material covers all surfaces of the piezo actuator. Overmolding in this manner advantageously provides controlled dimensions at the end of the piezo actuator. In certain embodiments, a urethane material cast directly to the actuator also compensates for nonuniformity in the actuator surface. Urethane over the entire actuator helps prevent water from accessing high voltage components.

In certain aspects, a smaller and cheaper actuator based off an all ceramic design can be used as opposed to composite designs that contain internal metal layers. Current actuators contain an all-ceramic outer layer and are inherently water resistant. Waterproofing is achieved in certain aspects by covering, painting or coating the piezo surfaces with a hydrophobic material. Examples of useful hydrophobic material include urethane (gasket material) and various spray-on epoxy coatings.

The embodiments herein advantageously provide the flow control with low power consumption and minimized fluid pressure drops, small size, reduced part count, and easy to service valve seats (the designs support both serviceable and non-serviceable actuators). Flow channels and orifices in the various embodiments are optimized to reduce pressure drops to the 10's of Pa's. Also, the piezo actuators are inherently fast as well, with natural frequencies of the actuators typically being between 60 and 120 Hz.

The embodiments described herein advantageously provide for low power dissipation and self heating, which provides improved temperature control of the fluid flowing within the passageways of the flow control assembly module. Each fluid, e.g., gas, stream is sensitive to heating effects of various device components. As a change in temperature results in a change in density of the fluid stream, even a small change in temperature can cause noticeable errors in measurements. Hence, the embodiments provided herein provide for enhanced control of flow rates and fluid diversion without disturbing the temperature of the fluids.

The various embodiments also advantageously provide easier access to the piezo elements and valve seats, e.g., for cleaning contaminants from the valves seats, benders, passageways, etc.

It should be appreciated that, although the examples of the flow control assembly module 25 described above include specific flow control configurations, other flow control configurations are within the scope of this disclosure.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the embodiments (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All method or process steps described herein can be performed in any suitable order unless otherwise indicated herein or otherwise clearly contradicted by context. The use of any and all examples, or exemplary language (e.g., "such as") provided herein, is intended merely to better illuminate the various embodiments and does not pose a limitation on the scope of the various embodiments unless otherwise claimed. No language in the specification should be construed as indicating any non-claimed element as essential to the practice of the various embodiments.

Exemplary embodiments are described herein. Variations of those embodiments may become apparent to those of ordinary skill in the art upon reading the foregoing description. The inventors expect skilled artisans to employ such variations as appropriate, and the inventors intend for the embodiments to be practiced otherwise than as specifically described herein. Accordingly, all modifications and equivalents of the subject matter recited in the claims appended hereto are included as permitted by applicable law. Moreover, any combination of the above-described elements in all possible variations thereof is encompassed unless otherwise indicated herein or otherwise clearly contradicted by context.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

The invention claimed:

1. A fluid valve assembly module comprising:
   a housing structure including a plurality of ports and a plurality of fluid passageways interconnecting the ports; and
   a plurality of piezo-actuated valves in fluid communication with the fluid passageways, each valve including a piezo element that controls flow along a passageway;
   wherein the passageways and valves are arranged within the housing structure so as to define a fluid control module comprising:
   a flow swapping component having first and second inlets and first and second output ports wherein the flow swapping component is configured to receive a first fluid flow at the first inlet and a second fluid flow at the second inlet and in a first operational mode to direct the first fluid flow to the first output port and the second fluid flow to the second output port, and in a second operational mode to direct the first fluid flow to the second output port and the second fluid flow to the first output port;
   a flow splitting component having an input port, a third output port and a first outlet wherein the flow splitting component is configured to receive an input fluid flow at the input port and to control an amount of the input fluid flow provided to the third output port and to the first outlet in a continuously adjustable manner, wherein the first outlet is fluidly connected to the first inlet of the flow swapping component and the third output port is adapted to be fluidly coupled with an external reservoir; and
   a flow pressurization component having an entry port in fluid communication with a second outlet, wherein the flow pressurization component is configured to receive a third fluid flow at the entry port and to control the pressure of the third fluid flow at the second outlet, wherein the second outlet is fluidly connected to the second inlet of the flow swapping component and the entry port is adapted to be fluidly coupled with the external reservoir.

2. The fluid valve assembly module of claim 1, wherein the flow swapping component includes two piezo elements, wherein the flow splitting component includes a single piezo element and wherein the flow pressurization component includes a single piezo element.

3. The fluid valve assembly module of claim 1, wherein each piezo element includes a cantilevered piezoelectric element that bends in response to an applied voltage signal.

4. The fluid valve assembly module of claim 3, wherein the piezo elements are arranged in a substantially planar side-by-side relationship.

5. The fluid valve assembly module of claim 3, wherein the piezo elements are arranged in a vertical stacked relationship.

6. The fluid valve assembly module of claim 3, wherein the fluid control module receives control signals from a control circuit external to the fluid control module.

7. The fluid valve assembly module of claim 6, further including a flow sensor connected between the third output port and the reservoir, wherein the flow sensor provides feedback signals to the control circuit.

8. The fluid valve assembly module of claim 1, wherein each piezo element includes a bi-morph piezo bender element.

9. The fluid valve assembly module of claim 8, wherein exposed surfaces of the piezo bender elements are coated with a hydrophobic material.

10. The fluid valve assembly module of claim 1, wherein the housing structure includes first and second structural layers comprising the plurality of passageways, and a third structural layer comprising the plurality of piezo elements, wherein the third layer is sandwiched between the first and second layers so as to form an integrated structure.

11. The fluid valve assembly module of claim 10, wherein one or both of the first and second layers includes integrated amplifier and control electronics adapted to control operation of the piezo elements in response to control signals received from an external control system.

12. The fluid valve assembly module of claim 10, wherein the piezo elements are bonded in place using a conductive adhesive.

13. The fluid valve assembly module of claim 1, wherein the piezo valves provide for passage of fluid with a low pressure drop and with low power dissipation.

14. The fluid valve assembly module of claim 1, wherein the flow splitting component is configured to provide, in a continuously adjustable manner, between 0% and 100% of the input fluid flow to the third output port and concomitantly the remainder of the input fluid flow to the first outlet.

15. A gas exchange analysis system, comprising:
   a gas source;
   a chamber defining a measurement volume for analysis of a sample;
   a first gas analyzer;
   a second gas analyzer; and a valve assembly module including a housing structure having a plurality of ports that fluidly interconnect the gas source, the chamber, the first gas analyzer and the second gas analyzer, wherein the valve assembly module includes a plurality of passageways interconnecting the ports and a plurality of valves that control fluid flow along the passageways, wherein the passageways and valves are arranged within the housing structure to define:
- a flow splitting component that receives an input fluid flow from the gas source and is configured to adjust an amount of the input fluid flow provided to both a flow swapping component as a first fluid flow and to the chamber;
- a flow pressurization component that is configured to, responsive to a control signal, actively control a pressure of a second fluid flow along a flow path from the chamber to the flow swapping component; and
- the flow swapping component that receives the first fluid flow and the second fluid flow along separate flow paths and that is configured to swap/interchange the first and second fluid flows between the first and second gas analyzers.

16. The system of claim 15, wherein:
the flow splitting component has an input port fluidly coupled with the gas source, a first output port fluidly coupled with the chamber and a first outlet fluidly connected to a first inlet of the flow swapping component, wherein the flow splitting component is configured to adjust the amount of the input fluid flow provided to both the first output port and the first outlet; and
the flow pressurization component has an entry port in fluid communication with the chamber, and a second outlet fluidly connected to a second inlet of the flow swapping component, wherein the flow pressurization component is configured to receive a second fluid flow from the chamber at the entry port and to control a pressure of the second fluid flow at the second outlet; and
the flow swapping component includes the first and second inlets, and second and third output ports fluidly coupled with the first and second gas analyzers, respectively, wherein the flow swapping component is configured to receive the first fluid flow at the first inlet and the second fluid flow at the second inlet and in a first operational mode to direct the first fluid flow to the second output port and the second fluid flow to the third output port, and in a second operational mode to direct the first fluid flow to the third output port and the second fluid flow to the second output port.

17. The system of claim 15, wherein the plurality of valves comprise a plurality of piezo-actuated valves in fluid communication with the fluid passageways, each valve including a piezo element that controls flow along a passageway.

18. The system of claim 17, wherein the flow swapping component includes two piezo elements, wherein the flow splitting component includes a single piezo element and wherein the flow pressurization component includes a single piezo element.

19. The system of claim 17, wherein each piezo element includes a cantilevered piezoelectric element that bends in response to an applied voltage signal.

20. The system of claim 17, wherein the piezo elements are arranged in a substantially planar side-by-side relationship.

21. The system of claim 17, wherein the piezo elements are arranged in a vertical stacked relationship.

22. The system of claim 17, wherein each piezo element includes a bi-morph piezo bender element.

23. The system of claim 22, wherein exposed surfaces of the piezo bender elements are coated with a hydrophobic material.

24. The system of claim 17, wherein then piezo valves provide for passage of fluid with a low pressure drop and with low power dissipation.

25. The system of claim 17, wherein the housing structure includes first and second structural layers comprising the plurality of passageways, and a third structural layer comprising the plurality of piezo elements, wherein the third layer is sandwiched between the first and second layers so as to form an integrated structure.

26. The system of claim 25, wherein one or both of the first and second layers includes integrated amplifier and control electronics adapted to control operation of the piezo elements in response to control signals received from an external control system.

27. The system of claim 15, further including a fluid control circuit that receives control signals from a control circuit external to the fluid control module.

28. The system of claim 27, wherein the flow splitting component includes a first output port fluidly coupled with the chamber, the system further including a flow sensor connected between the first output port and the chamber, wherein the flow sensor provides feedback signals to the fluid control circuit.

29. The system of claim 15, wherein the gas source provides a flow of carbon dioxide, and wherein the sample includes a tissue capable of photosynthesis.

30. The system of claim 15, wherein the flow splitting component is configured to provide, in a continuously adjustable manner, between 0% and 100% of the input fluid flow to the first output port and concomitantly the remainder of the input fluid flow to the first outlet.

* * * * *